United States Patent [19]

Cocherell et al.

[11] Patent Number: 5,004,596

[45] Date of Patent: * Apr. 2, 1991

[54] ANHYDROUS TOOTHPASTE OR DENTAL CREAM COMPOSITION

[76] Inventors: Francis E. Cocherell, 809 Silver Maple Dr., Azusa; Homer C. Harper, 15102 E. Chetney, Baldwin Park, both of Calif. 91702; George Hsieh, 23943 Sunset Crossing Rd., Covina, Calif. 91765

[*] Notice: The portion of the term of this patent subsequent to Mar. 14, 2006 has been disclaimed.

[21] Appl. No.: 297,172

[22] Filed: Jan. 17, 1989

Related U.S. Application Data

[63] Continuation-in-part of Ser. No. 139,064, Dec. 21, 1987, Pat. No. 4,812,306, which is a continuation of Ser. No. 819,583, Jan. 17, 1986, abandoned.

[51] Int. Cl.$^5$ .............. A61K 7/26; A61K 7/18
[52] U.S. Cl. ........................... 424/52; 424/49; 424/56; 424/58
[58] Field of Search ....................... 424/49–58

[56] References Cited

U.S. PATENT DOCUMENTS 3,937,804  2/1976  Delaney .................. 424/52
4,159,315  6/1979  Wagenknecht .......... 424/48
4,812,306  3/1989  Cocherell ................ 424/52

Primary Examiner—F. T. Moezie

[57] ABSTRACT

A water-free dental cream or toothpaste composition comprising 6% to 90% by total weight of one or more hydrogenated vegeteable oils, 0.02% to 25% by total weight of one or more flavoring oils or extracts, 0.1% to 60% by total weight of glycerin, 0.5% to 25% by total weight of cornstarch, 10% to 90% by total weight of one or more inorganic salts selected from the group comprising sodium bicarbonate, magnesium sulfate and sodium chloride, 0.001% to 3.5% by total weight of more or more fluorides selected from the group comprising sodium fluoride, potassium fluoride and ammonium fluoride, 0.01% to 5% by total weight of saccharin or aspartame, and 0.01% to 5% by total weight of sodium lauryl sulfate.

7 Claims, No Drawings

ANHYDROUS TOOTHPASTE OR DENTAL CREAM COMPOSITION

CROSS REFERENCE TO RELATED APPLICATION

The present application is a continuation-in-part of co-pending application Ser No. 139,064, filed Dec. 21, 1987, now U.S. Pat. No. 4,812,306 which was a continuation of Ser. No. 819,583, filed Jan. 17, 1986 now abandoned.

FIELD OF THE INVENTION

The present invention generally relates to a dentrifice composition and more particularly to a water-free dental cream or toothpaste wherein a non-humectant, anhydrous binder is present as a carrier for a chemotherapeutic inorganic salt, particularly, non-ionic sodium bicarbonate. The carrier is comprised of one or more hydrogenated vegetable oils.

BACKGROUND OF THE INVENTION

Teeth are very unique in the human body in that they are the only body tissue that are not subject to metabolic turnover. Once our permanent teeth are formed, theoretically they are almost indestructible. For this reason, it is easy to understand the important role of teeth in archeological diggings since they are preserved in the fossil records. Another area in which teeth play an important role is in the area of forensic dentistry.

In spite of their seemingly indestructible nature, teeth are constantly subjected to bacterial attack throughout a person's lifetime. Such bacterial attack manifests itself in the form of various periodontal diseases including dental caries. Periodontal disease ranks as the most universal affliction suffered by mankind. As of 1977, it was estimated that, in the United States alone, the cost of treating various periodontal diseases exceeded 11 billion dollars.

Bacterial plaque has been shown to be a leading cause of disease of the teeth and of the periodontium. Plaque results from the interaction of mucin, a conjugated protein present in human saliva, with various micro-organisms present throughout the oral flora. Bacterial plaque causes decalcification of the enamel layer of the tooth structure. The disintegration of enamel is accomplished by both enzymes as well as acids formed from the bacterial colonies within the plaque.

Several specific species of micro-organisms have been implicated in the human periodontal disease during recent studies. The micro-organisms which are present in subgingival plaque are believed to play in important role as agents in causing this destructive disease. A small group of mostly gram positive anaerobic bacteria, from more than 200 morphologically and biochemically distant species which have been isolated from human periodontal pockets, has been closely related with diseased sites exhibiting inflamation, destruction of the periodontal attachment and crestal alveolar bone. Included within this group are strains of oral spirochetes, *Bacteriodes gingivalis, Bacteroides intermedius, Fusobacterium numcleatum, Ekenella corrodens, Eubacteriym sp, Actinobacillus actinomycetemcomitans, Selennomnonas sputigena,* and *Wolinella recta.*

The above micro-organisms have been shown to be present in periodontal lesion and have been shown to possess potentially pathogenic virulence factors which account for their attachment and proliferation below the tissue. Furthermore, they inhibit host defense mechanisms while creating periodontal tissue damage.

Other recent studies have shown that sodium bicarbonate, as well as other inorganic salts such as sodium chloride and magnesium sulfate, have beneficial therapeutic properties when used as a chemotherapeutic agent for treatment of oral micro-organisms associated with periodontal disease. These inorganic salts were shown to be rapidly bacteriocidal to oral spirochetes and motile rods by inducing, after brief in vitro exposure, ultrastructural changes toxic to periodontal disease organisms. These anti-microbial agents were active against all suspected periodontopathogens tested. Sodium bicarbonate at a concentration of 84,000 ppm was found to produce in vitro a 99% lethality to selected strains of B intermedium and F nucleatum within 15 to 30 minutes after exposure.

The use of pure sodium bicarbonate has already been proven very effective in the removal of dental plaque and has also been shown to be effective in the control of periodontal disease. Sodium bicarbonate in powder form has been used for a number of years, however, it has never gained widespread acceptance by the public since it is inconvenient and difficult to use in powder form. At present, there is no sodium bicarbonate toothpaste on the market that is available for consumer use.

SUMMARY AND OBJECTS OF THE INVENTION

The present invention fulfills a long-felt but previously unsolved need by incorporating sodium bicarbonate as well as other inorganic salts into a water-free or anhydrous dental cream or toothpaste composition for use as a chemotherapeutic agent in the treatment of oral micro-organisms associated with periodontal disease. The invention further includes the use of one or more hydrogenated oils as a carrier or medium for the sodium bicarbonate or other inorganic salts. The use of hydrogenated oils is essential in that they do not chemically react with the sodium bicarbonate. Sodium bicarbonate, when in the presence of small amounts of water, will give off carbon dioxide gas forming sodium carbonate and carbonic acid. As sodium carbonate is much more alkaline than sodium bicarbonate, it adds a very bitter taste which is very difficult to mask in a toothpaste. All previous toothpaste preparations have been comprised of an aqueous mixture using a humectant with water present in varying quantities. The use of hydrogenated oils allows the present toothpaste preparation to be water-free, thereby preventing the formation of undesirable sodium carbonate.

The dental cream or toothpaste of the present invention is prepared by combining flavoring oils and glycerin to form a liquid mixture, thickening the liquid mixture by the addition of starch, e.g., corn starch U.S.P. or wheat flour U.S.P., kneading the thickened mixture to form a dough-like mass and subsequently drying the dough-like mass. After sufficient drying, the dough-like mass becomes dry and crumbly and is subsequently ground to form a powder. The powder is then mixed with one or more inorganic salts as well as with other dry ingredients including fluoride, a sweetener such as aspartame or saccharin, and sodium lauryl sulfate to form a powder mixture which is combined with one or more hydrogenated oils and whipped until a cream or paste of the desired consistency is obtained.

It is therefore an object of the present invention to provide a water-free dental cream or toothpaste composition including one or more chemotherapeutic inorganic salts.

Another object of the present invention is to provide a method of incorporating a liquid masking or flavoring agent into a dental cream or toothpaste composition without changing the viscosity of a hydrogenated binder of the product and without eventual separation of the flavoring oils.

A still further object of the present invention is to provide a water-free dental cream or toothpaste which is stable in nature with regard to the active ingredients.

Another object of the present invention is to provide a novel method of preparing a stable water-free dental cream or toothpaste.

These and other objects and advantages of the present invention will become apparent in view of the following detailed description.

DETAILED DESCRIPTION OF THE INVENTION

In a preferred embodiment, the water-free cream or toothpaste composition is comprised of between about 6% and 90% by total weight of one or more hydrogenated vegetable oils, between about 0.20% and 25% by total weight of one or more flavoring oils including oil extracts, between about 0.1% and 60% by total weight of glycerin, between about 0.5% and 25% by total weight of cornstarch, between about 10% and 90% by total weight of one or more inorganic salts, between about 0.001% and 3.5% by total weight of one or more fluorides, between about 0.01% and 5% by total weight of sodium lauryl sulfate.

Cottonseed oil, sunflower oil, soybean oil, corn oil, coconut oil, mineral oil, rapeseed oil and glycerin thickened with a gelling agent are satisfactory candidates for an anhydrous carrier for the sodium bicarbonate and other ingredients in this toothpaste formula. A preferred carrier comprises vegetable oils partly hydrogenated to a soft solid state to remove the need for a gelling agent. The ideal partly hydrogenated oils are soybean oil, cottonseed oil and palm oil. These oils are commercially available for the food industry. They are offered in blends that are designed for outstanding flavor, stability, shelf life and a wide plastic range and workability.

The melting point of the candidate hydrogenated oil should fall between 110 degrees F. and 120 degrees F.; AOM stability should be 60 hours, plus or minus 5; flavor, bland; Lovibond color red, max. 2.0; and an Iodine value of 75 to 80 meq. maximum. ADM Packaged Oils of Decatur, Ill. manufactures an all purpose shortening, 101-050, that meets the required analysis and characteristics. The wide plastic range and workability of a hydrogenated oil of these specifications makes it ideally suited for blending the solid ingredients of this tooth paste. The finished product comes from the tube easily and is of a consistency that retains its form on the bristles of the tooth brush. The melting point that is slightly higher than the temperature of the oral cavity holds the solid ingredients of the tooth paste in suspension while the teeth are being brushed insuring that excellent contact can be made with the teeth. The white color of the partly hydrogenated oils increases the whiteness of the tooth paste, and the bland flavor enhances the taste of the flavoring oils.

The flavor of a tooth paste is an important ingredient in determining if the public will accept or reject the product. No single flavoring oil will mask the taste of the sodium bicarbonate and/or other salts used in this formula. The flavoring oils or oil extracts may include anise oil, sassafras, peppermint, eugenol and Pemiento Gordo berry extract. Eugenol is a principal ingredient in the Pemiento Gordo berry and is very important in masking the taste of the salts in this tooth paste formula. Pemiento Gordo is a berry of the Myrtle tree or shrub family. This berry is common in the tropical regions of Central America and an analysis of its oil indicates it is different from other berrys of this tree family from which all-spice is derived. The present formula that has been developed for this tooth paste may use the foregoing flavoring oils to successfully mask the taste of the salts therein and leave a pleasant, clean, and invigorating sensation in the oral cavity. Sweeteners such as aspartame and saccharin may also be added.

The invention also provides a method of incorporating the flavoring oils into the final product in a solid form so that they will not leach out of the hydrogenated oil carrier. The flavoring oils are mixed with glycerin which itself acts as a flavoring agent since it has a sweet taste; glycerine is also a good antiseptic. The mixed glycerol (glycerin) and flavoring oils are converted into a solid form by, first, mixing with starch, which is kneaded to form a dough like mass, which mass is allowed to dry and subsequently ground into a powder.

Starch has been useful to man for thousands of years as food, as a powder for hair, in laundry to stiffen clothes, for sizing paper and other uses such as absorbing indicators in chemical tests and many other uses. Starch is present in all assimilating plants but the great bulk of the starch is always found in the food reservoirs of the plants, e.g., rhizomes, tubers, and seeds. This is known as reserve starch and it is from such sources that starch is manufactured commercially. Starch forms a white velvety hygroscopic powder consisting of round or elongated granules built up of concentric layers around a nucleus or hilum and the form and size of the granules vary considerably with starches from different sources. The largest granules are from canna, potato, banana and sago starch and are about 60 microns; those from lentils, corn, acorn and wheat are intermediate and those from certain millets, oats, and rice are smallest, or about 15 microns. In wheat starch the granules are nearly spherical and the hilum in the center; those of potato are egg or oyster shaped with an eccentric hilum at the small end of the granule, and those from rice and corn are polygonal.

Potatoes contain 15-20% starch, wheat and corn 60-65% and rice 75-80%. There are other sources of starch such as arrowroot starch from the rhizomes of Maranta of the West Indies and Curcuma Augustifolia of the East Indies, and sago starch from the sago palm and tapioca from the tubers of the cassava. There are also other sources not mentioned herein. Corn starch was chosen for this invention because of its availability and purity but other starches from other sources could have been used such as the flours of wheat, rice, potatoes and so on.

Sodium lauryl sulfate is used in an amount which will minimize its action as a foaming agent when the tooth paste of this invention is being applied to the teeth by a tooth brush but which amount is sufficient to facilitate the removal of the tooth paste from the tooth brush by rinsing in cold water after completion of brushing. In this regard, it is desireable to minimize the foaming action on the teeth since that would tend to inhibit the deposit of a film of the active ingredients of the tooth paste or cream on the teeth.

The inorganic salts may include sodium bicarbonate, magnesium sulfate and sodium chloride. In the case of sodium bicarbonate, which should be in the molecular form of monoclinic white crystalline prisms, optimum therapeutic results have been achieved when about 20% of the sodium bicarbonate particles are about 40 microns in diameter and the remaining 80% of particles vary in size from about 40 microns down to about 1 micron or less in diameter. Such a particle size distribution maximizes cleaning efficiency without causing harmful tooth abrasion.

The fluorides may includes sodium fluoride, potassium fluoride and ammonium fluoride.

If it is desired that sodium bicarbonate not be the sole abrasive, it is also possible to incorporate into the above toothpaste or dental cream composition between about 5% and 25% of a suitable silica abrasive.

|  | % By Weight |
|---|---|
| EXAMPLE I |  |
| Anise Oil U.S.P. | 1.481 |
| Clove Oil U.S.P. | .206 |
| Sassafrass U.S.P. | .823 |
| Peppermint U.S.P. | 1.646 |
| Glycerin U.S.P. | 11.695 |
| Cornstarch U.S.P. | .247 |
| Sodium Fluoride | .247 |
| Sodium Saccharin | .617 |
| Sodium Lauryl Sulfate | .617 |
| Sodium Bicarbonate | 35.076 |
| Hydrogenated Vegetable Oil | 46.769 |
| EXAMPLE II |  |
| Glycerin U.S.P. | 1.81 |
| Anise Oil U.S.P. | 2.57 |
| Eugenol U.S.P. | 0.16 |
| Sassafras U.S.P. | 1.60 |
| Peppermint U.S.P. | 0.16 |
| Spearmint U.S.P. | 0.24 |
| Wintergreen U.S.P. | 0.16 |
| Cornstarch U.S.P. | 11.52 |
| Sodium BiCarbonate | 34.10 |
| Sodium Lauryl Sulfate | 0.80 |
| Sodium Saccharin | 1.20 |
| Sodium Fluoride | 0.16 |
| Hydrogenated Soybean Oil | 45.52 |
|  | 100.00% |

The water-free dental cream or toothpaste composition of either example is prepared by combining the flavoring oils or oil extracts with glycerin to form a liquid mixture, adding corn starch to the liquid mixture to form a thickened mixture, and kneading the thickened mixture to form a dough-like mass. The dough-like mass is placed into an air-tight container and allowed to dry at about 115° to 125° F. for approximately 8 to 12 hours. As drying occurs, the flavoring oils are absorbed by the corn starch and the dough-like mass turns lighter in color. After the drying period, absorption of the flavoring oils is complete and the dough-like mass turns into a dry, crumbly material which is not crystalline in nature. The now dried material is ground into a powder and combined with the remaining dry ingredients including the fluorides, saccharin or aspartame, sodium lauryl sulfate and the inorganic salts. This powder mixture is then whipped together with the hydrogenated oils until a cream or paste having the desired consistency is obtained.

By following the above procedure, a stable dental cream or toothpaste mixture is obtained. Since no water is present in the formulation, the inorganic salts including sodium bicarbonate do not undergo adverse chemical changes. Furthermore, the flavoring oils or oil extracts having been converted into powder form are prevented from separating out of the hydrogenated oils. The conversion of the flavoring oils into a powder form does not adversely affect their flavoring qualities.

A comparison was made of pure sodium bicarbonate, three leading commercially available toothpastes and the foregoing Example I of the present invention, based on the hypothesis that the longer after use that an alkaline pH remained in the mouth the longer the active ingredients were still effective. In the case of the three commercial toothpastes there was a relatively short period of rise in pH after brushing, to about 7 or 8. The pH then subsided to a baseline level of about 5, which was normal for the subject studied in this comparison, after a period of about 10-12 minutes. In the case of pure sodium bicarbonate a sharp rise in pH to a higher level (about 9) was detected, the subject's pH level then declining more gradually than in the case of the commercial toothpastes to about a normal pH of 5 at the expiration of 50 minutes after brushing In the case of Example I of this invention, the subject's pH rose sharply to about 9 and the effects of the higher pH remained for a much longer period of time than in the case of the commercial pastes or pure sodium bicarbonate, the alkalinity gradually descending to a pH of 6.6 180 minutes after brushing. This was probably due a microscopic film or layer containing non-ionic sodium bicarbonate on the teeth and soft tissues which was slowly released into its ionic form thus creating a sustained relatively high pH level.

While this invention has been described in connection with different embodiments thereof, it will be understood that it is capable of further modifications, and this application is intended to cover any variations, uses, or adaptations of the invention following, in general, the principles of the invention and including such departures from the present disclosure as come within known or customary practice in the art to which the invention pertains, as may be applied to the essential features hereinbefore set forth and followed in the scope of the invention or the limits of the appended claims.

We claim:

1. A chemically stable anhydrous tooth paste or dental cream composition of;
   (a) a powdery mixture comprising about 10% to about 90% by total weight of the composition of one or more anhydrous inorganic salts selected from the group consisting of sodium bicarbonate, magnesium sulfate and sodium chloride, about 0.02% to about 25% by total weight of the composition of a flavoring oil, about 0.1% to about 60% by total weight of the composition of glycerin, and about 0.2% to about 25% by total weight of the composition of a powdery absorbent, said flavoring oil and said glycerin being present in said powdery mixture in solid form absorbed into said absorbent, and
   (b) said powdery mixture being uniformly present in about 6% to about 90% by total weight of the composition of a vegetable oil carrier that has been sufficiently hydrogenated to provide cream or paste consistency to the composition.

2. The composition according to claim 1 wherein said flavoring oil is selected from the group consisting of anise oil, clove oil, sassafrass, peppermint, eugenol, Pemiento Gordo and mixtures thereof.

3. The composition according to claim 1 wherein said absorbent is selected from the group consisting of cornstarch and wheat flour.

4. The composition according to claim 1 further comprising about 0.001% to about 3.5% by total weight of the compound of a fluoride providing compound selected from the group consisting of sodium fluoride, potassium fluoride and ammonium fluoride.

5. The composition according to claim 1 further comprising a sweetener selected from the group consisting of saccharin and aspartame.

6. The composition according to the claim 1 further comprising about 0.01% to about 5% by total weight of the composition of sodium lauryl sulfate.

7. The composition according to claim 1 wherein the vegetable oil carrier is selected from the group consisting of sunflower oil, soybean oil and coconut oil.

* * * * *